(12) United States Patent
Garza

(10) Patent No.: US 9,987,398 B2
(45) Date of Patent: Jun. 5, 2018

(54) PATTERN TRANSFER DEVICE FOR MASS TRANSFER OF MICRO-PATTERNS ONTO MEDICAL DEVICES

(71) Applicant: PALMAZ SCIENTIFIC, INC., Fremont, CA (US)

(72) Inventor: Armando Garza, San Jose, CA (US)

(73) Assignee: VACTRONIX SCIENTIFIC, LLC, Fremont, CA (US)

( * ) Notice: Subject to any disclaimer, the term of this patent is extended or adjusted under 35 U.S.C. 154(b) by 0 days. days.

(21) Appl. No.: 15/245,030

(22) Filed: Aug. 23, 2016

(65) Prior Publication Data

US 2017/0049940 A1 Feb. 23, 2017

Related U.S. Application Data

(63) Continuation of application No. 14/197,513, filed on Mar. 5, 2014, now Pat. No. 9,422,633, which is a
(Continued)

(51) Int. Cl.
*C25F 3/14* (2006.01)
*C25F 7/00* (2006.01)
(Continued)

(52) U.S. Cl.
CPC ............... *A61L 31/14* (2013.01); *A61L 31/00* (2013.01); *B23H 3/04* (2013.01); *B23H 9/00* (2013.01);
(Continued)

(58) Field of Classification Search
CPC ..... C25F 7/00; C25F 3/14; B23H 9/14; B23H 3/04
See application file for complete search history.

(56) References Cited

U.S. PATENT DOCUMENTS 1,318,487 A 10/1919 Donaldson
2,375,481 A 5/1945 Lee et al.
(Continued)

FOREIGN PATENT DOCUMENTS

EP 0 734 699 10/1996 ............... A61F 2/06
EP 0 850 604 7/1998 ............... A61F 2/06
(Continued)

OTHER PUBLICATIONS

Chehroudi, et al., "Titanium-coated micromachined grooves of different dimensions affect epithelial and connective-tissue cells differently in vivo" *Journal of Biomedical Materials Research* 24(9): 1203-1219 (1990).
(Continued)

*Primary Examiner* — Nicholas A Smith
(74) *Attorney, Agent, or Firm* — David G. Rosenbaum; Benjamin D. Rotman; Rosenbaum IP, P.C.

(57) ABSTRACT

This invention is directed to a pattern transfer device and assembly for mass-transfer/fabrication of micro-sized features/structures onto the inner diameter (ID) surface of a stent. This new approach is provided by technique of through mask electrical micro-machining. One embodiment discloses an application of electrical micro-machining to the ID of a stent using a customized electrode configured specifically for machining micro-sized features/structures.

12 Claims, 10 Drawing Sheets

Related U.S. Application Data continuation of application No. 13/663,808, filed on Oct. 30, 2012, now Pat. No. 8,668,818, which is a continuation of application No. 12/914,467, filed on Oct. 28, 2010, now Pat. No. 8,329,021.

(51) Int. Cl.

| | |
|---|---|
| *B23H 9/14* | (2006.01) |
| *B23H 3/04* | (2006.01) |
| *A61L 31/14* | (2006.01) |
| *B23H 9/00* | (2006.01) |
| *C25F 3/02* | (2006.01) |
| *A61L 31/00* | (2006.01) |
| *A61F 2/82* | (2013.01) |

(52) U.S. Cl.
CPC ............ *B23H 9/008* (2013.01); *B23H 9/14* (2013.01); *C25F 3/02* (2013.01); *C25F 3/14* (2013.01); *C25F 7/00* (2013.01); *A61F 2/82* (2013.01); *A61F 2240/001* (2013.01)

(56) References Cited

U.S. PATENT DOCUMENTS

| | | | |
|---|---|---|---|
| 2,557,722 A | 6/1951 | Brauchler | |
| 2,618,182 A | 11/1952 | Teetor | |
| 3,122,830 A | 3/1964 | Dawson et al. | |
| 4,100,388 A | 7/1978 | Meyer | 219/69 |
| 4,425,696 A | 1/1984 | Torniainen | 29/157.3 |
| 4,437,327 A | 3/1984 | Madden | 72/94 |
| 5,102,417 A | 4/1992 | Palmaz | 606/195 |
| 5,772,864 A | 6/1998 | Moller et al. | 205/73 |
| 5,824,052 A | 10/1998 | Khosravi et al. | 623/1 |
| 5,824,053 A | 10/1998 | Khosravi et al. | 623/1 |
| 5,843,172 A | 12/1998 | Yan | 623/1 |
| 5,855,802 A | 1/1999 | Acciai et al. | 216/8 |
| 5,893,887 A | 4/1999 | Jayaraman | 623/1 |
| 5,902,475 A | 5/1999 | Trozera et al. | 205/655 |
| 6,001,124 A | 12/1999 | Bachinski | 623/1 |
| 6,007,573 A | 12/1999 | Wallace et al. | 623/1 |
| 6,019,784 A | 2/2000 | Hines | 623/1 |
| 6,190,404 B1 | 2/2001 | Palmaz et al. | 623/1.15 |
| 6,379,528 B1 | 4/2002 | Lee | 205/640 |
| 6,586,699 B1 | 7/2003 | Gianchandani et al. | 219/69.17 |
| 6,663,765 B2 | 12/2003 | Cherkes | 205/668 |
| 2001/0050235 A1 | 12/2001 | MacLeod | 205/640 |
| 2002/0017503 A1 | 2/2002 | Banas et al. | 219/69.11 |
| 2002/0023843 A1 | 2/2002 | Cherkes | 205/75 |
| 2002/0025248 A1* | 2/2002 | Lee | B23H 9/00 415/1 |
| 2005/0230266 A1 | 5/2005 | Callol et al. | 205/640 |
| 2009/0071837 A1* | 3/2009 | Fredenberg | B81C 99/0085 205/131 |
| 2009/0082854 A1 | 3/2009 | Cherkes | 623/1.42 |
| 2009/0093879 A1 | 4/2009 | Wawro et al. | 623/11.11 |
| 2009/0192593 A1 | 7/2009 | Meyer et al. | 623/1.42 |
| 2009/0277803 A1 | 11/2009 | Wei | 205/665 |

FOREIGN PATENT DOCUMENTS

| | | | | |
|---|---|---|---|---|
| EP | 0 974 314 | | 1/2000 | A61F 2/06 |
| JP | 58-188519 | | 11/1983 | B21D 17/00 |
| JP | 11-042283 | | 2/1999 | A61M 29/00 |
| JP | 2002-511779 | | 4/2002 | A61M 29/02 |
| WO | WO 1999/23977 | | 5/1999 | A61F 2/06 |
| WO | WO 1999/61261 | | 12/1999 | B44C 1/22 |
| WO | WO 2000/10623 | | 3/2000 | A61L 31/14 |
| WO | WO 2001/00112 | | 1/2001 | A61F 2/06 |
| WO | WO 2006093605 A1 * | 9/2006 | B23H 3/04 |
| WO | WO 2006/107382 | | 10/2006 | H01M 4/02 |

OTHER PUBLICATIONS

Kathuria, Y.P., "The potential of biocompatible metallic stents and preventing restenosis" *Materials Science and Engineering* 417(1-2): 40-48 (2006).
Lee, E.S., et al., "A Study on electrochemical micromachining for fabrication of microgrooves in an air-lubricated hydrodynamic bearing" *International Journal of Advanced Manufacturing Technology* 20:720-726 (2002).
Lee, E.S., et al., "Investigation of short pulse electrochemical machining for groove process on Ni-Ti shape memory alloy" *International Journal of Precision Engineering and Manufacturing* 11(1): 113-118 (2010).
Mineta, T., et al., "Characteristics of the electrochemical etching of TiNi-shape memory alloy in a LiCl-ethanol solution" *Journal of Micromechanics and Microenoineering* 20: 1-8 (2010).
Mineta, T., "Electrochemical etching of a shape memory alloy using new electrolyte solutions" *Journal of Micromechanics and Microengineering* 14: 76-80 (2004).
PCT International Search Report, pp. 1-6 (dated Jun. 26, 2012).
PCT Written Opinion, pp. 1-4 (dated Jun. 26, 2012).
Takahata, K., "Micro-electro-discharge machining technologies for MEMS" *In-Tech Croatia* ISBN 978-953-307-027-8 pp. 143-164 (2009).
EP Extended Search Report and Search Opinion, EP Application No. 11837131.9, pp. 1-8 (dated Jan. 5, 2018).

* cited by examiner

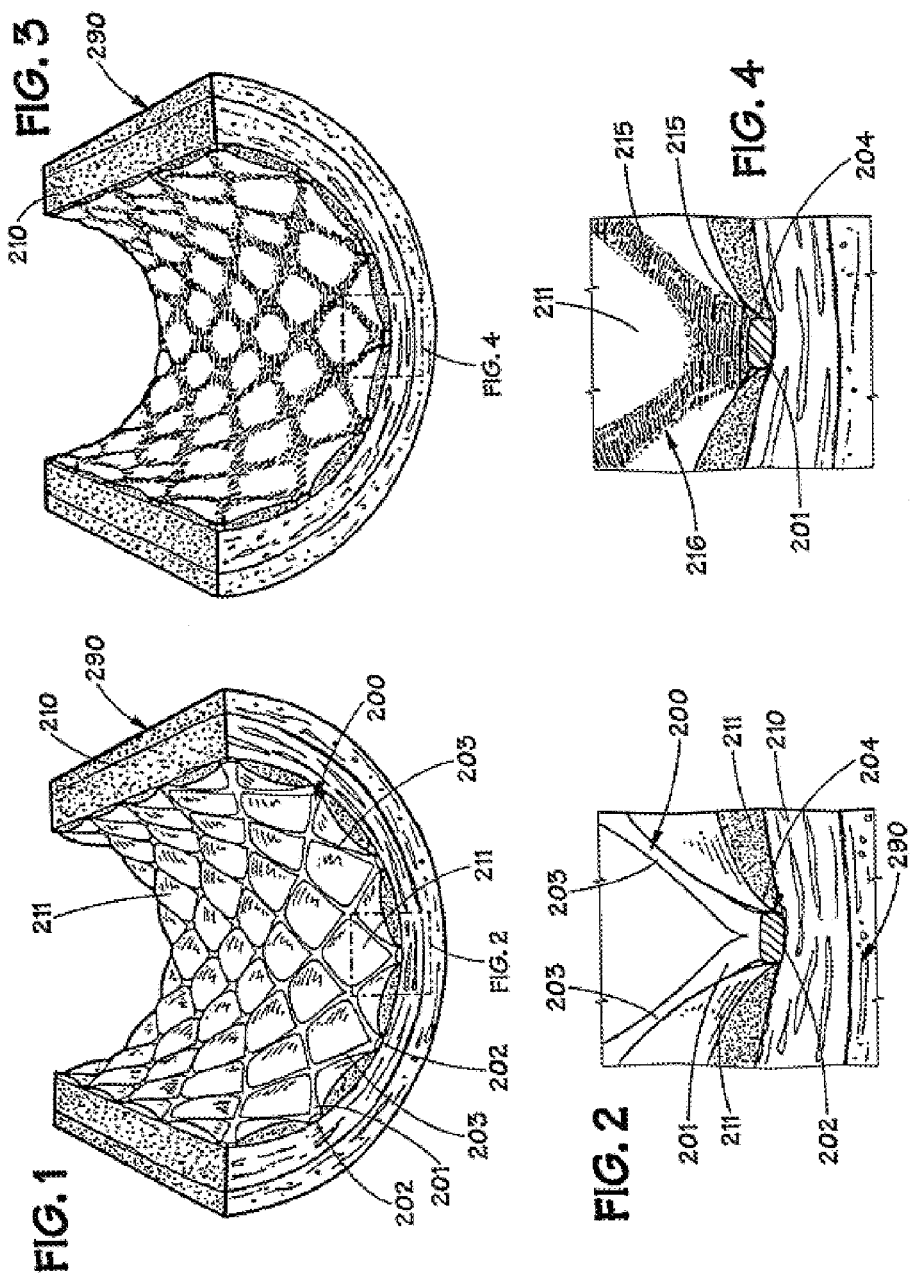

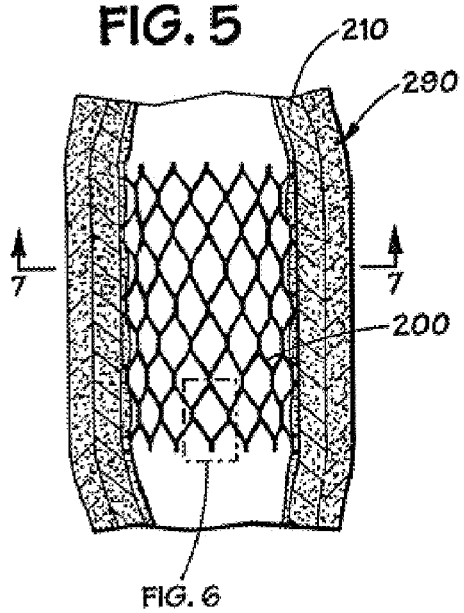
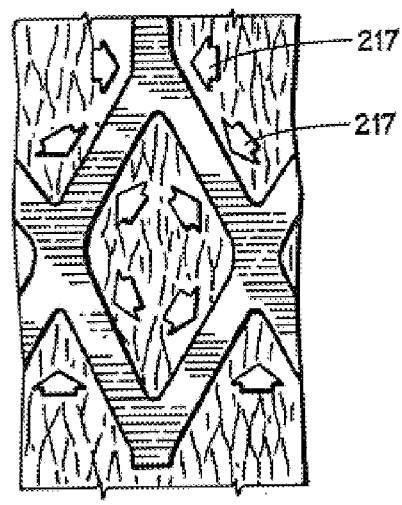
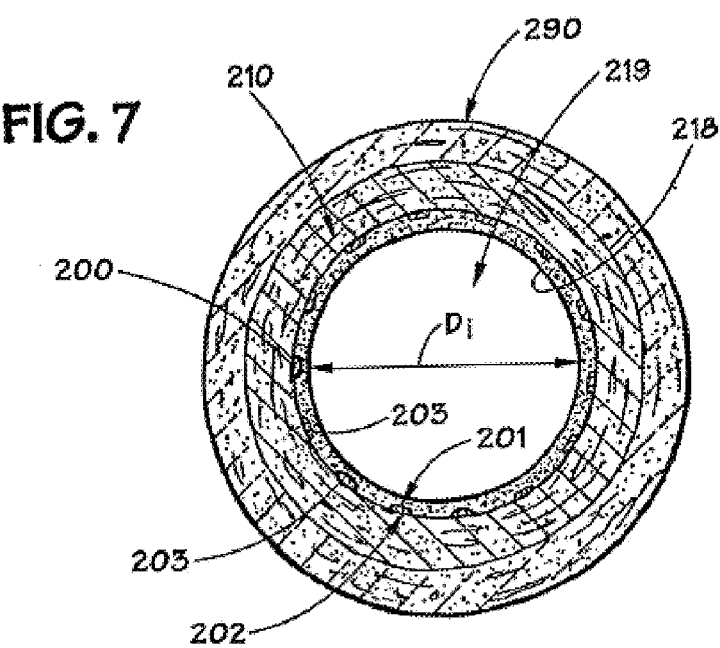

PATTERN TRANSFER DEVICE FOR MASS TRANSFER OF MICRO-PATTERNS ONTO MEDICAL DEVICES

CROSS-REFERENCE TO RELATED APPLICATION

This application is a continuation of U.S. patent application Ser. No. 14/197,513, filed Mar. 5, 2014, which will issue as U.S. Pat. No. 9,422,633 on Aug. 23, 2016; which is a continuation of U.S. patent application Ser. No. 13/663,808, filed Oct. 30, 2012, now U.S. Pat. No. 8,668,818, issued on Mar. 11, 2014; which is a continuation of U.S. patent application Ser. No. 12/914,467, filed on Oct. 28, 2010, now U.S. Pat. No. 8,329,021 issued on Dec. 11, 2012, all herein incorporated in their entireties.

BACKGROUND OF THE INVENTION

This invention generally relates to therapeutic tissue engineering devices for the treatment of Ischemic Diseases. More specifically, the present application relates to a process of electrochemically machining micro-sized micro-pattern structures onto the inner diameter of a Balloon eXpanding (Bx) or Self eXpanding (Sx) stent.

Alternative techniques that may be employed to fabricate micro-sized features on the inner diameters of medical devices include direct laser ablation, metal stamping/pressing, and photolithography/wet etching. It is believed that none of these techniques have the potential for use either in part or entirely in the fore-mentioned process to accomplish micro-sized features on the inner diameter of the medical device. The present invention solves these problems as well as others.

SUMMARY OF THE INVENTION

Provided herein are methods and systems for mass-transfer/fabrication of micro-sized features/structures onto the inner diameter surface of a stent. The method of producing micro-patterns on a medical device generally comprises providing a metal electrode cathode, a non-conducting mask coating the outer diameter of the metal electrode and a medical device anode; attaining the non-conducting mask by coating the metal electrode cathode; patterning desired features on the mask and then transferring the desired features to the medical device anode by electrochemical micromachining. In one embodiment, this method involves the use of an electrode/non-conducing mask/stent assembly.

The methods and systems are set forth in part in the description which follows, and in part will be obvious from the description, or can be learned by practice of the methods, compositions, and systems. In one embodiment, the new approach is provided by technique of through mask electrochemical micro-machining. The present application discloses an application of electrochemical micro-machining to the inner diameter of a stent using a customized electrode configured specifically for machining micro-sized features/structures.

BRIEF DESCRIPTION OF THE FIGURES

FIG. 1 is a partial cross-sectional perspective view of a portion of a intravascular stent embedded within an arterial wall of a patient;

FIG. 2 is an exploded view of the outlined portion of FIG. 1 denoted as FIG. 2;

FIG. 3 is a partial cross-sectional, perspective view corresponding to FIG. 1 after the passage of time;

FIG. 4 is an exploded view of the outlined portion of FIG. 3 denoted as FIG. 4;

FIG. 5 is a partial cross-sectional view of the stent and artery of FIGS. 1 and 3 after a further passage of time;

FIG. 6 is an exploded view of the outlined portion of FIG. 5 denoted as FIG. 6;

FIG. 7 is a partial cross-sectional view of the stent and artery of FIG. 5, taken along lines 7-7 of FIG. 5, and illustrates rapid endothelialization resulting in a thin neointimal layer covering the stent;

DETAILED DESCRIPTION OF THE PREFERRED EMBODIMENTS

Figure 8A:
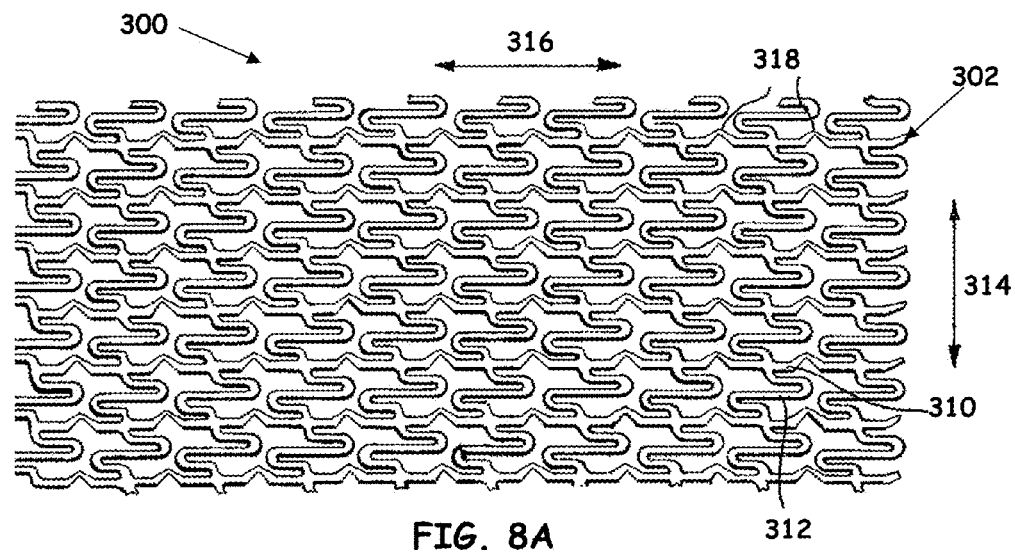
FIG. 8A is a side elevational view of an intravascular stent.

The foregoing and other features and advantages of the invention are apparent from the following detailed description of exemplary embodiments, read in conjunction with the accompanying drawings. The detailed description and drawings are merely illustrative of the invention rather than limiting, the scope of the invention being defined by the appended claims and equivalents thereof.

With reference to FIGS. 1 and 2, an intravascular stent 200 is illustrated being disposed within an artery 290 in engagement with arterial wall 210. For illustrative purposes only, intravascular stent 200, shown in FIGS. 1-6 is a Palmaz™ balloon-expandable stent, as is known in the art, stent 200 having an inner diameter 201 and an outer diameter 202. FIGS. 1 and 2 illustrate stent 200 shortly after it has been placed within artery 290, and after stent 200 has been embedded into arterial wall 210, as is known in the art. FIGS. 1 and 2 illustrate what may be generally characterized as correct placement of an intravascular stent. Stent 200 preferably includes a plurality of metal members, or struts, 203, which may be manufactured of stainless steel, or other metal materials, as is known in the art. As illustrated in FIGS. 1 and 2, correct placement of stent 200 results in tissue mounds 211 protruding between the struts 203, after struts 203 have been embedded in the arterial wall 210. Struts 203 also form troughs, or linear depressions, 204 in arterial wall 210. Dependent upon the degree of blockage of artery 290, and the type and amount of instrumentation utilized prior to placement of stent 200, the mounds of tissue 211 may retain endothelial cells (not shown). machined pattern may include features which pin or demote cell proliferation. These patterns may be used to steer cells to control a directionality of healing response. Any type of cell is encompassed by the present invention, which have a cellular membrane. Most distinct cell types arise from a single totipotent cell that differentiates into hundreds of different cell types during the course of development. Multicellular organisms are composed of cells that fall into two fundamental types: germ cells and somatic cells. During development, somatic cells will become more specialized and form the three primary germ layers: ectoderm, mesoderm, and endoderm. After formation of the three germ layers, cells will continue to specialize until they reach a terminally differentiated state that is much more resistant to changes in cell type than its progenitors. The ectoderm differentiates to form the nervous system (spine, peripheral nerves and brain), tooth enamel and the epidermis (the outer part of integument). It also forms the lining of mouth, anus, nostrils, sweat glands, hair and nails. The endoderm forms the gastrointestinal tract cells, the respiratory tract cells, the endocrine glands and organ cells, the auditory system cells, and the urinary system cells. The mesoderm forms mesenchyme (connective tissue), mesothelium, non-epithelial blood cells and coelomocytes. Mesothelium lines coeloms; forms the muscles, septa (cross-wise partitions) and mesenteries (length-wise partitions); and forms part of the gonads (the rest being the gametes).

Alternative medical devices may be employed with the grooves disclosed herein, such as grafts, filters, implants, temporary implants such as a vena cava filter or an insulin pump needle, bone grafts, dental implants, heart valves or electrical leads, temporary tubing, or any other device where grooves may be needed or cell growth is required.

With reference to FIGS. 3 and 4, after the passage of time, a thin layer of thrombus 215 rapidly fills the depressions 204, and covers the inner diameters 201 of stent 200. As seen in FIG. 4, the edges 216 of thrombus 215 feather toward the tissue mounds 211 protruding between the struts 203. The endothelial cells which were retained on tissue mounds 211 can provide for reendothelialization of arterial wall 210.

With reference to FIGS. 5 and 6, endothelial regeneration of artery wall 210 proceeds in a multicentric fashion, as illustrated by arrows 217, with the endothelial cells migrating to, and over, the struts 203 of stent 200 covered by thrombus 215. Assuming that the stent 200 has been properly implanted, or placed, as illustrated in FIGS. 1 and 2, the satisfactory, rapid endothelialization results in a thin tissue layer 218, as shown in FIG. 7. As is known in the art, to attain proper placement, or embedding, of stent 200, stent 200 must be slightly overexpanded. In the case of stent 200, which is a balloon-expandable stent, the balloon diameter chosen for the final expansion of stent 200 must be 10% to 15% larger than the matched diameter of the artery, or vessel, adjacent the site of implantation. As shown in FIG. 7, the diameter Di of the lumen 219 of artery 290 is satisfactory. If the reendothelialization of artery wall 210 is impaired by underexpansion of the stent or by excessive denudation of the arterial wall prior to, or during, stent placement, slower reendothelialization occurs. This results in increased thrombus deposition, proliferation of muscle cells, and a decreased luminal diameter Di, due to the formation of a thicker neointimal layer.

Figure 8B:
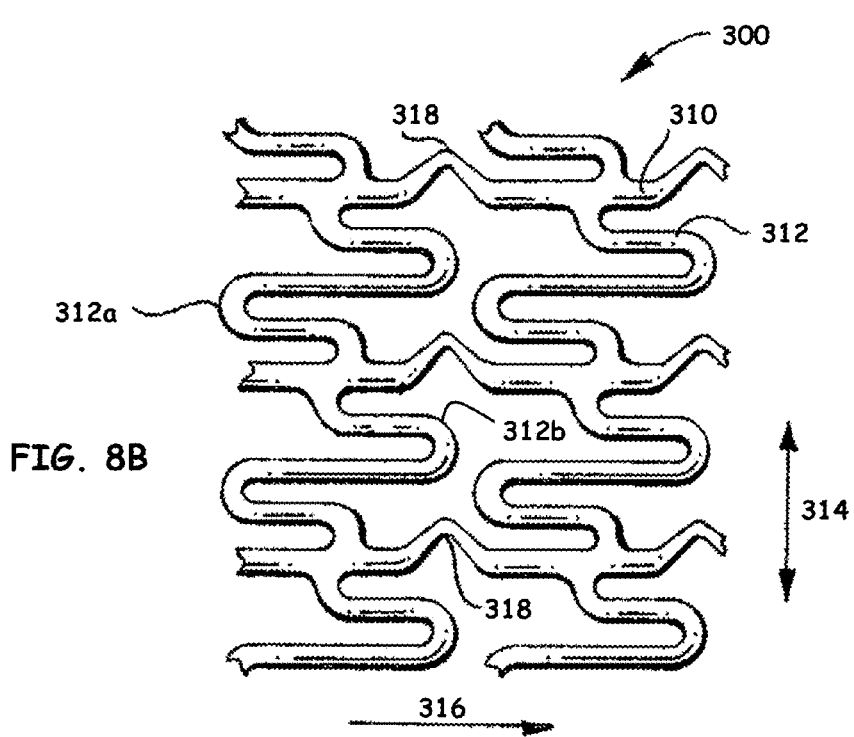
FIG. 8B is an enlarged perspective view of a portion of the intravascular stent of FIG. 8A.

With reference to FIGS. 8A and 8B, an intravascular stent 300 in accordance with one embodiment is illustrated. For illustrative purposes only, the structure of intravascular stent 300 is illustrated as being a Palmaz™ balloon-expandable stent, as is known in the art, illustrated in its initial, unexpanded configuration. It should be understood that the improvement of the embodiments disclosed herein is believed to be suitable for use with any intravascular stent having any construction or made of any material as will be hereinafter described. Similarly, the improvement of the embodiments disclosed herein in methods for manufacturing intravascular stents is also believed to be applicable to the manufacturing of any type of intravascular stent as will also be hereinafter described.

In one embodiment, the intravascular stent 300 consists generally of a tubular cylindrical element having a stent wall that defines an inner diameter 301 and an outer diameter 302 of the stent. As shown in FIGS. 8A and 8B, a plurality of first structural elements 310 are arrayed about the circumferential axis 314 of the stent 300 and extend generally parallel along the longitudinal axis 316 of the stent 300. A plurality of second structural elements 312 are oriented generally parallel to the circumferential axis 314 of the stent 300 and interconnect adjacent pairs of the plurality of first structural elements 310. Each of the plurality of second structural elements 312 have a generally sinusoidal configuration with at least one complete sine curve, i.e., having both positive and negative amplitude in the proximal and distal directions relative to the longitudinal axis 316 of the intravascular stent 300, being subtended between adjacent pairs of the first structural elements 310. A plurality of peaks 312a and a plurality of troughs 312b are formed in each the second structural elements 312. The plurality of peaks 312a and the plurality of troughs 312b may have either regular or irregular periodicity along the longitudinal axis of each of the plurality of second structural elements 312 or each of the plurality of second structural elements 312 may have regions of regular periodicity and regions of irregular periodicity. A plurality of flex regions 318 are formed in each of the plurality of first structural members 310. Each of the plurality of flex regions 318 are formed as narrowed regions of the first structural element 310 and may have a V-shaped or sinusoidal configuration (shown in FIGS. 15 and 16) which project circumferentially from each of the plurality of first structural elements 310. It is contemplated that one of the plurality of flex regions 318 may be positioned intermediate adjacent pairs of the second structural elements 312 along the first structural element 310.

The plurality of first structural elements 310 and the plurality of second structural elements 312 are preferably made of materials selected from the group consisting of elemental titanium, vanadium, aluminum, nickel, tantalum, zirconium, chromium, silver, gold, silicon, magnesium, niobium, scandium, platinum, cobalt, palladium, manganese, molybdenum and alloys thereof, and nitinol and stainless steel. The plurality of first structural elements 310 and the plurality of second structural elements 312 may be made of the same material or of different materials and have the same material properties or have different material properties. The term material properties is intended to encompass physical properties, including, for example and not by way of limitation, elasticity, tensile strength, mechanical properties, hardness, bulk and/or surface grain size, grain composition, grain boundary size, and intra- and inter-granular precipitates. Similarly, the materials selected for the plurality of first structural elements 310 and the plurality of second structural elements 312 may be selected to have the same or different chemical properties. The term material properties is intended to encompass both any chemical reaction and change of state that the material may undergo after being implanted into a body and the physiological response of the body to the material after implantation.

As illustrated in FIG. 8A, intravascular stent, or stent, 300 has an inner diameter 301, and an outer diameter 302, outer diameter 302 normally being embedded into arterial wall 210 in an abutting relationship. In accordance with one embodiment, the inner diameter 301 of stent 300 is provided with a micro-pattern 400 (shown in FIG. 9). The micro-pattern 400 of one embodiment may be provided in, or on, the inner diameter or luminal surface 301 of stent 300 by mass transferring the micro-pattern(s) via through-mask electrochemical micro-machining (ECμM), as will be hereinafter described in greater detail. For illustrative purposes only, the micro-pattern is shown in FIGS. 9-21 as a plurality of linearly grooved structures. It should be understood that the micro-pattern can be provided in a wide array of shapes, structures, and patterns, such as, for example, and not by way of limitation, a wave structure, cross-hatched pattern, or concentric circles, as described more fully below. Stents generally have an inner diameter or luminal surface and an outer diameter or abluminal surface, i.e. the surface that contacts a lumen, blood vessel, cavity, and the like.

Figure 9:
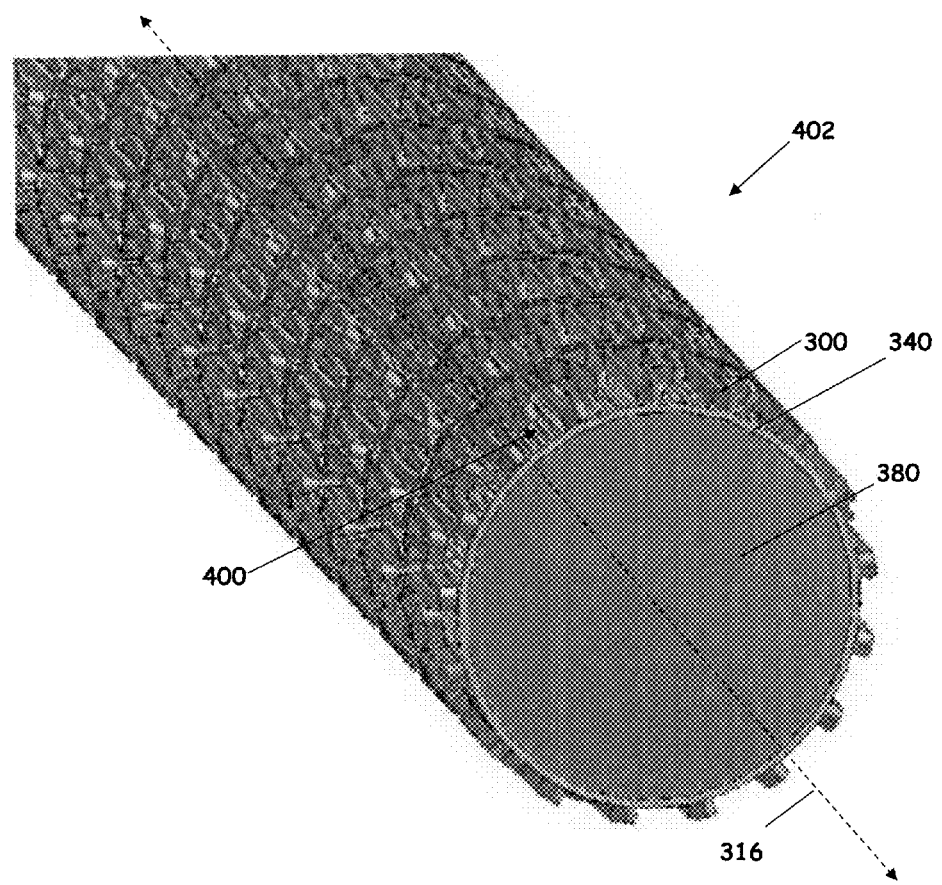
FIG. 9 is a perspective view of the micro-patterned electrode-implant configuration for electrochemical micromachining.
Figure 18:
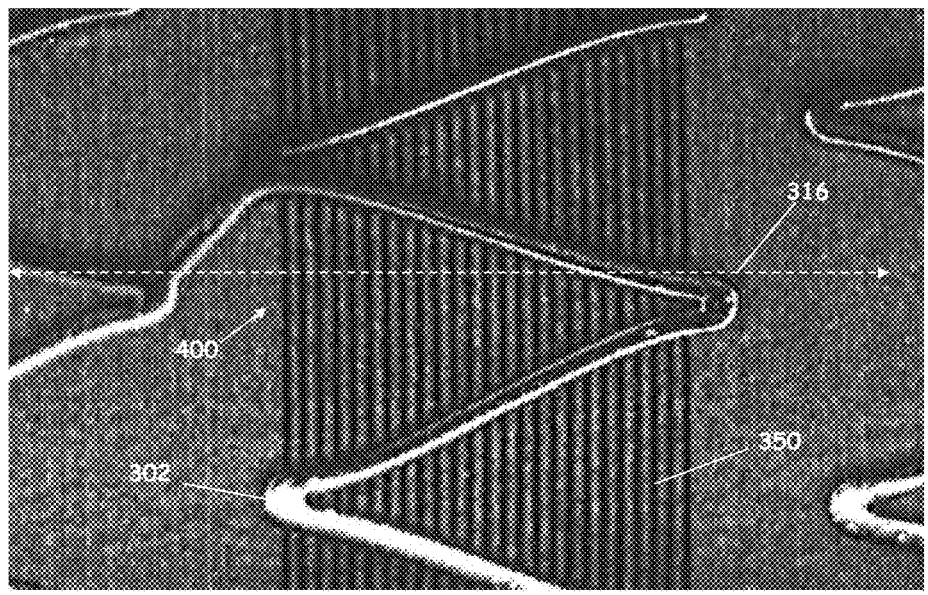
FIG. 18 is an enlarged perspective view of the micro-patterned pattern oriented in the circumferential direction with an electrode polymer thickness of about 25-40 µm.

As shown in FIG. 9, the micro-pattern 400 may be disposed with its longitudinal axis being disposed substantially parallel with the longitudinal axis 316 of stent 300, in accordance with one embodiment. Alternatively, the longitudinal axis of the micro-pattern 400 may be disposed substantially perpendicular to the longitudinal axis 316 of stent 300, as shown in FIG. 18; or the longitudinal axis of the micro-pattern may be disposed at an obtuse, or acute, angle with respect to the longitudinal axis 316 of stent 300. The angle that micro-pattern 400 makes with respect to longitudinal axis 316 is either an acute or an obtuse angle dependent upon from which direction the angle is measured with respect to the longitudinal axis 316 of stent 300. The selection of the angle of the micro-pattern 400 with respect to the longitudinal axis 316 may be selected according to the placement of medical device 300, type of endothelial cell, and/or direction of growth for the endothelial cell.

A plurality of micro-patterns 400 may be disposed on the inner diameter 301 of stent 300. The plurality of micro-patterns could be provided in a serpentine fashion or in a cross-hatched manner. It should be noted that the angular disposition and location of the plurality of micro-patterns 400 will vary and be altered upon the expansion of stent 300 within the artery 290 (FIG. 1), and the stent 300 being illustrated in its unexpanded configuration in FIG. 9. It should be further noted, as previously discussed, that the mass transfer of the micro-pattern, or micro-patterns, may be provided in, or on, the inner diameter of any intravascular stent, so as to increase the rate of migration of endothelial cells on, and over, the inner diameter of the intravascular stent.

In general, micro-pattern 400 has a width W, a depth D, and a length L. The width W and depth D may be the same, and not vary, along the length L of the micro-pattern 400. Alternatively, the width W of the micro-pattern may vary along the length L of the micro-pattern 400. Alternatively, the depth D of the micro-pattern may vary along the length L. Alternatively, both the width W and the depth D of the micro-pattern 400 may vary along the length L. Similarly, as with the location and angular disposition of micro-pattern, or micro-patterns, 400 as described in connection with FIG. 9, the width W, depth D, and length L of the micro-pattern, or micro-patterns, 400 can vary as desired, and different types of micro-patterns 400 could be disposed on the inner diameter 301 of stent 300.

Figure 10:
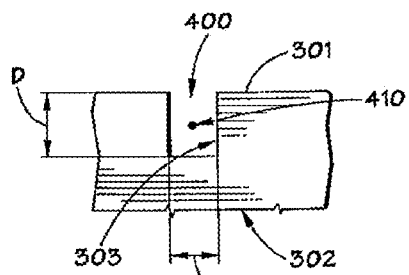
FIGS. 10-14 are various embodiments of an exploded view of a micro-pattern, illustrating various cross-sectional configurations and characteristics of various embodiments of the micro-pattern in accordance with one embodiment.
Figure 11:
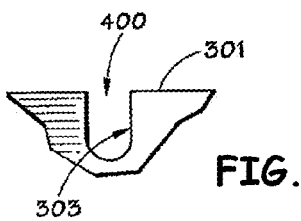
Figure 12:
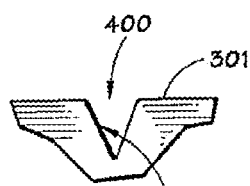
Figure 13:
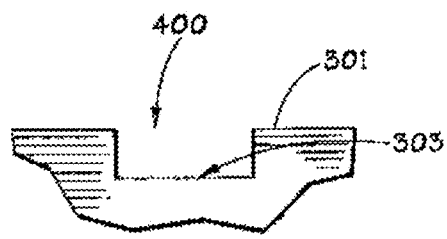
Figure 14:
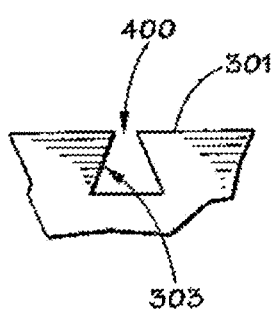

As desired, the cross-sectional configuration of the micro-pattern, or micro-patterns, 400 may vary along the length L of the micro-pattern(s); or the cross-sectional configuration of the micro-pattern may not vary along the length. The cross-sectional configuration of the micro-pattern, or micro-patterns, 400 may be substantially symmetrical about the longitudinal axis 410 of micro-pattern 400; or the cross-sectional configuration of the at least one micro-pattern may be substantially asymmetrical about the longitudinal axis 410. The cross-sectional configurations of micro-pattern 400 can assume a variety of shapes, and include those cross-sectional configurations which are substantially: square shaped (FIG. 10); U shaped (FIG. 11); triangular, or V shaped (FIG. 12); rectangular shape (FIG. 13); and triangular, or keyway shaped (FIG. 14). The wall surface 303 of each micro-pattern 400 may be substantially smooth.

The depth D of micro-pattern, or micro-patterns, 400 may fall within a range of approximately one-half to approximately ten microns. However, in no event should the depth D of micro-pattern, or micro-patterns, 400 exceed the distance between the inner diameter 301 and the outer diameter 302 of the stent 300. The width W of micro-pattern, or micro-patterns, 400, may fall within a range of approximately two to approximately forty microns. Of course, the width W and depth D could be varied from the foregoing ranges, provided the rate of migration of endothelial cells onto stent 300 is not impaired. The length L of micro-pattern 400 may extend the entire length of stent 300, such as micro-pattern 400 of FIG. 9; or the length L' of a micro-pattern may be less than the entire length of stent 300, such as micro-pattern 400 in FIG. 18. The micro-pattern, or micro-patterns, may be continuous, or discontinuous, along the length of the inner diameter 301 of stent 300.

The portion of the inner diameter 301 of stent 300 which has not been provided with a micro-pattern, or micro-patterns, 400 in accordance with one embodiment, may have any suitable, or desired, surface finish, such as an electropolished surface, as is known in the art, or may be provided with whatever surface finish or coating is desired. It is believed that when a micro-pattern 400 in accordance with one embodiment is disposed, or provided, on, or in, the inner diameter 301 of an intravascular stent 300, after the implantation of stent 300, the rate of migration of endothelial cells upon the inner diameter 301 of stent 300 will be increased over that rate of migration which would be obtained if the inner diameter 301 were not provided with a micro-pattern 400 in accordance with one embodiment.

To manufacture intravascular stents with a mass-transferred micro-pattern disposed in the inner diameter of the stent, one embodiment provides a method for mass transferring the micro-pattern onto the inner diameter of an intravascular stent via through-mask ECμM.

Figure 15:
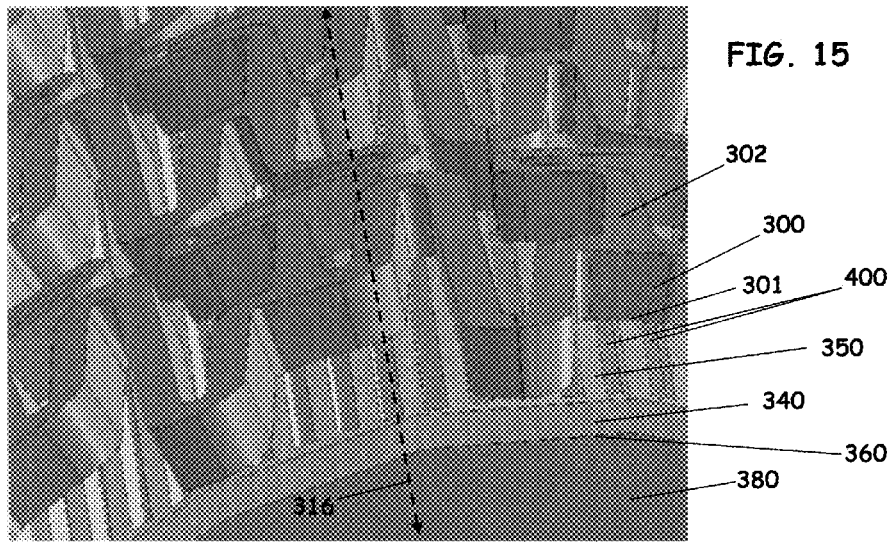
FIG. 15 is an enlarged perspective view of the end section of the micro-patterned electrode-stent configuration for electrochemical micro-machining, showing the stent/implant (+), patterned polymer/Non-conducting mask, and the metal electrode (−)
Figure 16:
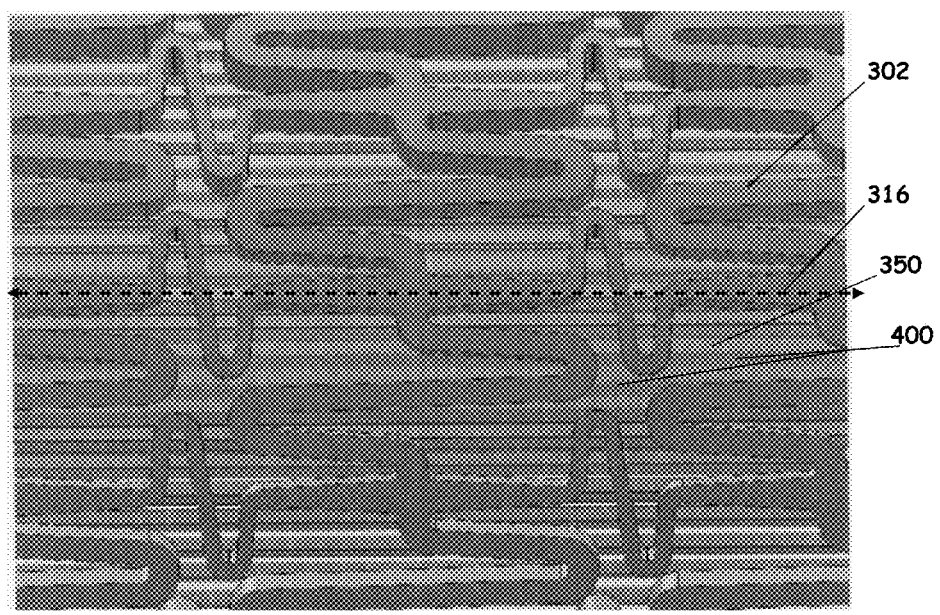
FIG. 16 is a perspective view of the middle section of the micro-patterned electrode-implant configuration for electrochemical micro-machining.

With reference to FIG. 9, the configuration of the micro-patterned intravascular stent/electrode through-mask ECμM assembly 402 comprises a metal electrode 380, a non-conducting mask 340 disposed on the outer diameter 360 of the electrode 380, and an intravascular stent/implant 300. The micro-patterned masked electrode/intravascular stent configuration for the through-mask ECμM process is also shown in FIGS. 16, and 18. The configurations shown in FIGS. 15 and 16 illustrate a masked electrode 350, oriented parallel to the longitudinal axis 316 of the stent 300, having a micro-pattern 400 that is also parallel to the longitudinal axis 316 of the intravascular stent 300. The configuration shown in FIG. 18 shows the masked electrode 350, oriented parallel to the longitudinal axis 316 of the stent 300, having a micro-pattern 400 that is perpendicular to the longitudinal axis 316 of the intravascular stent 300.

Figure 17:
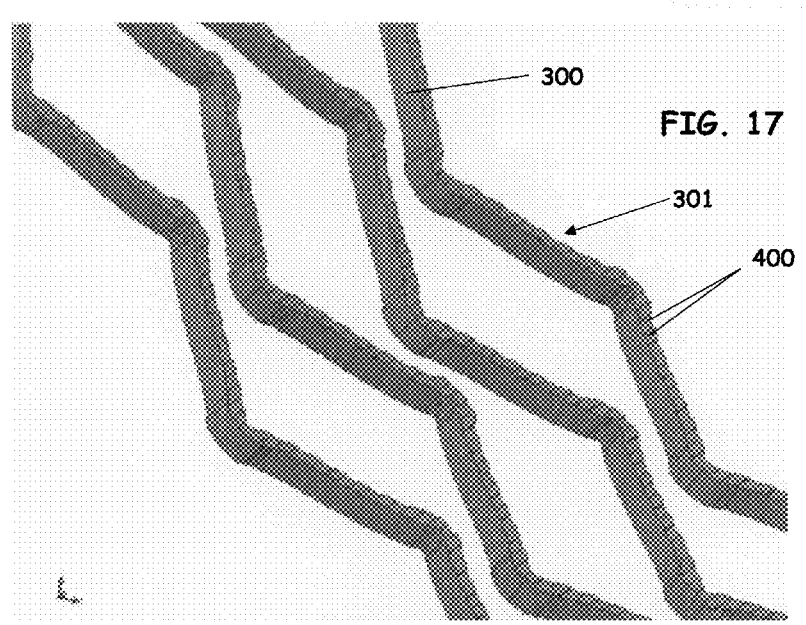
FIG. 17 is an enlarged perspective view of the micro-patterned stent/implant post electrochemical micromachining.
Figure 19:
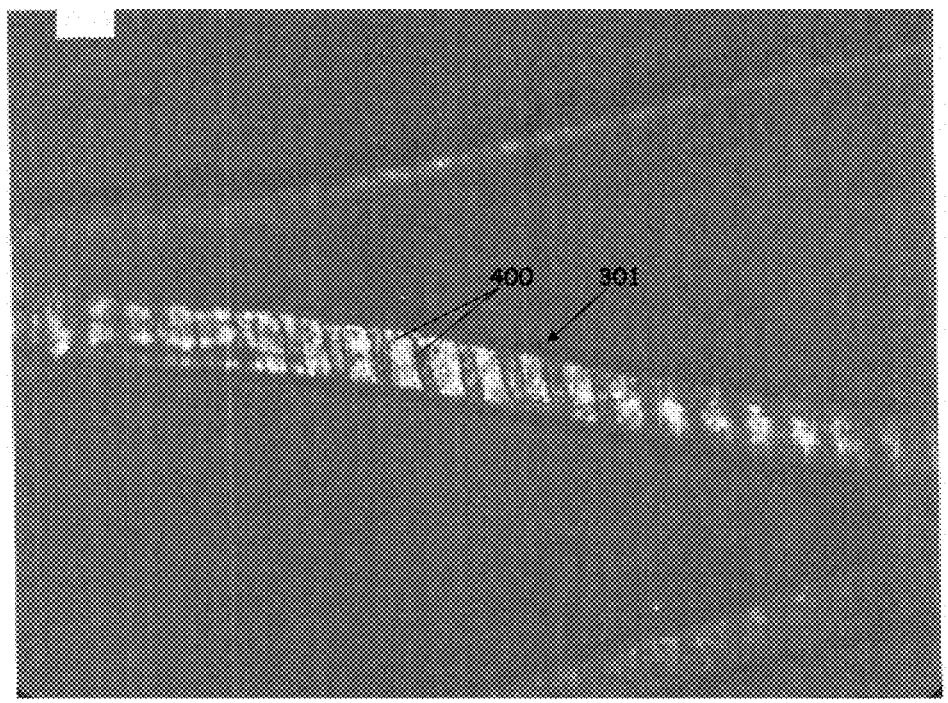
FIG. 19 is a photomicrograph at low magnification of the micro-pattern structure machined onto the inner diameter of the stent via electrochemical micro-machining.
Figure 20:
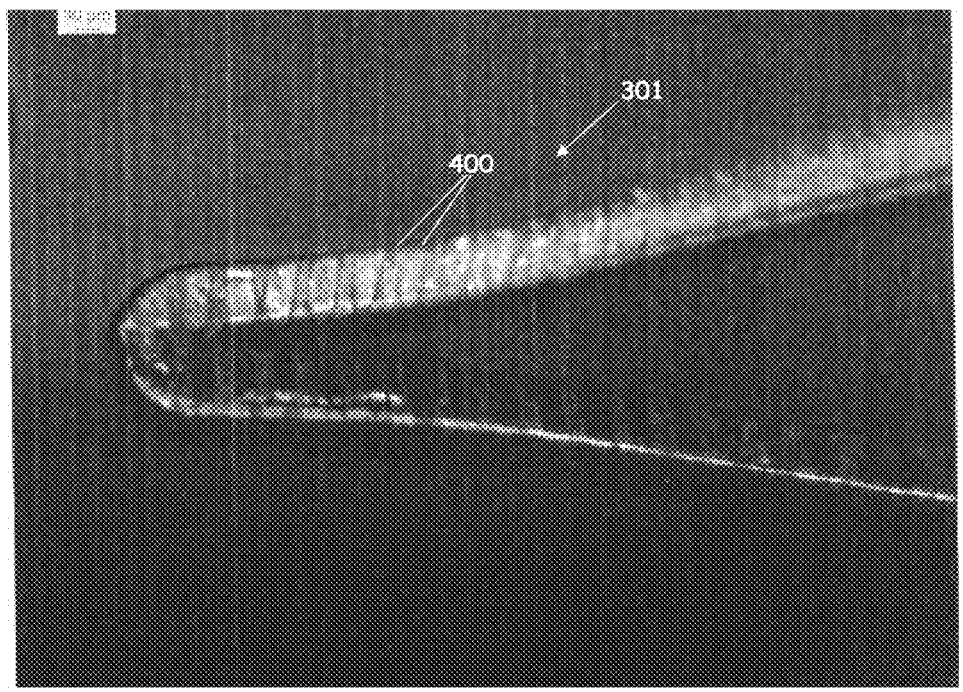
FIG. 20 is a photomicrograph at low magnification of the micro-pattern structure at a joint of the stent machined onto the inner diameter of the stent via electrochemical micro-machining.
Figure 21:
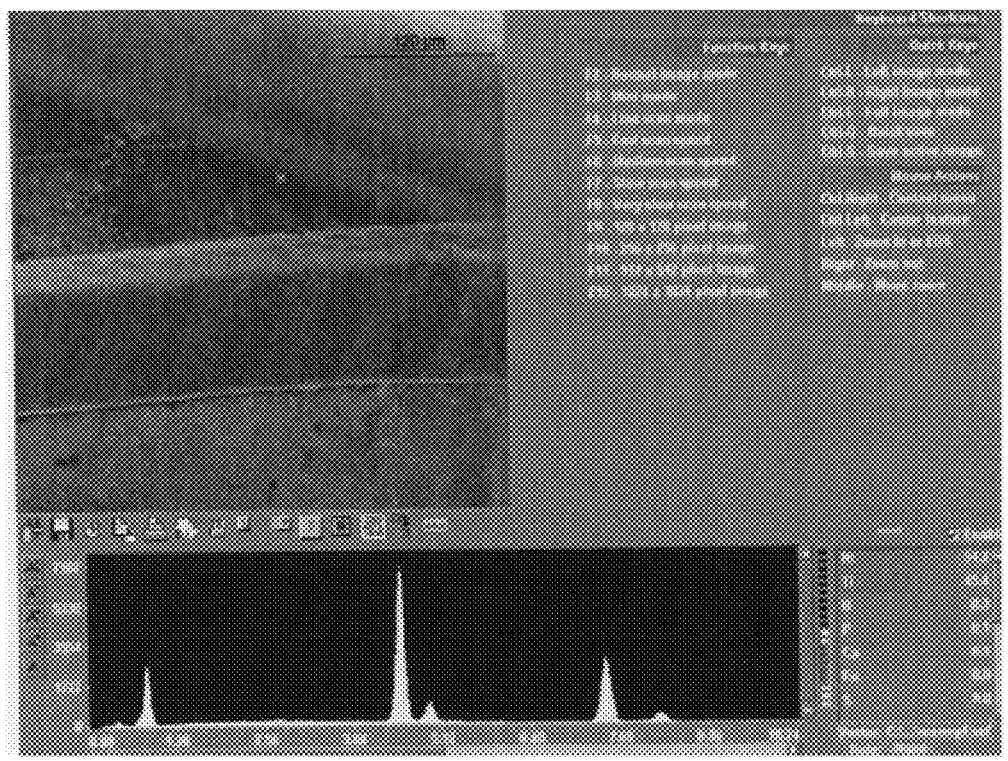
FIG. 21 is an electron image of the micro-pattern structures on the stent machined onto the inner diameter of the stent via electrochemical micro-machining.

As shown in FIG. 15, the through-mask ECμM process involves first attaining a masked-electrode 350 by coating an outer diameter 360 of a metal electrode 380 with a non-conducting mask 340, imparting a micro-pattern 400 on the outer diameter of the masked-electrode 350 via laser ablation or other techniques, mounting the intravascular stent 300 over the micro-patterned masked electrode 350, such that the inner diameter 301 of the stent 300 is in contact with the micro-patterned masked electrode 350, and then mass-transferring the micro-pattern 400 features on the outer diameter of the masked-electrode 350 onto the inner diameter 301 of the intravascular stent/implant 300 via through-mask ECμM 402. During the machining process, direct or pulsed currents, voltages and/or a combination thereof, are applied for a specified amount of time or charge before the assembly is removed from the electrolyte solution, washed and dried. Then, the intravascular stent 300 is removed from the masked electrode 350 and, upon inspection; the inner diameter 301 of the stent 300 will display a micro-pattern 400, as shown in FIGS. 17, 19, and 20.

The displayed micro-pattern features on the inner diameter 301 of the intravascular stent 300 is a result of micro-machining through distinctly defined channels of electrical current such that when a potential is applied between the masked electrode 350 and the inner diameter 301 of the stent 300, only those areas exposed to these current channels will undergo oxidative processes M0(s)+electrons→M+(aq). The defined channels are essentially the conductive pathways through which dissolution will take place. The channel bounded on one side by the masked electrode 350 and on the other side by the inner diameter 301 of the stent 300 defines the "machining gap" as used herein. The size of the machining gap is largely a function of the feature size(s) imparted on the patterned electrode and thus, can vary from application to application. For example, the working relationships for machining micro-sized micro-patterns that are relatively shallow to promote endothelial function may be different from larger features designed to load therapeutic agents. Machining is rendered exclusive to only those surfaces of the intravascular stent 300 most proximal to the electrode 380, in-turn rendering the distal surfaces 302 of the stent 300, which essentially see insufficient current densities to initiate active dissolution, passive (no dissolution) during the machining process. In general, the dimensional attributes of all machining gaps, electrode pattern, target pattern on implant etc., are likely to be within the same order of magnitude of each other. A regime of machining parameters may be selected to be coupled with the construction of the stent/electrode assembly to allow for the active machining to occur at sites most proximal to the counter electrode surface, which would be though the machining gap.

Rate of Machining is the rate at which different metals can be machined depends on the amount of current passed and the duration for which it is passed. The interelectrode distance (machining gap) will have some play in the electrical current distribution and thus, may affect the machining rate to some extent.

Pulsed current in Electrochemical machining conventionally utilizes DC input as power source. Alternative techniques however employ high frequency pulsed voltage to reach better resolutions. The applied voltage waveform plays a crucial role in defining a profile quality and surface finish of microECM'ed part. With the use of ultrahigh frequency inputs around GHz range, electrochemical reactions are restricted to electrode regions in close proximity which exceeds far beyond the 0.1 mm limited spatial resolution defined solely by electrolytic current density in DC voltages. Machining is performed during pulse-on time and pulse-off time is kept long enough to dissipate heated electrolyte and produced gas formed during pulse-on time. With higher frequencies, the machined cavity diameter converges to the tool diameter. On the other hand, increased amplitude would increase the removed material for a given time, since more electrons are driven with more power supplied.

Although the material removal rate may be dictated by the reaction rate, the flushing away of the reaction products from the machining zone is also important for efficient machining. The selection of the ideal flow patterns and velocity was paramount for obtaining the best results. The gradient in the flow path directly affected the surface finish and depth of cut. The ability to transfer micro-sized features onto the ID of the stent was achieved via a simple immersion of the stent/electrode assembly into the electrolyte with gentle stirring of peripheral electrolyte. A more forced agitation within the machining gap may be employed in other embodiments.

MicroECM setups mostly have actuation mechanisms for repeatable machining. Two types of actuation are possible on a setup and they define types of control mechanisms as well: open-loop and closed-loop controls. The positioning system may be either open or closed loop.

The metal electrode 380, which can be made from components of stainless steel, brass, copper, graphite, molybdenum, silver, tungsten, platinum, etc., is coated or modified to render its outer diameter 360 electrically non-conductive. This can be accomplished by coating the outer diameter 360 of the metal electrode 380 with a polymer, ceramic, oxide or any other electrically non-conductive material. Polymers of, for example, and not by way of limitation, phenol and its derivatives, phenylenediamines, and overoxidized or electroinactive polypyrrole can be used as the non-conductive coating material. The coating process can be carried out by dipping, spray coating, air brush, lamination or other chemical or physical vapor deposition techniques.

This non-conducting layer 340, with a thickness ranging from hundreds of angstrom up to microns, preferably the thickness is between about 25 μm to 40 μm, is then patterned before the inner diameter 301 of the intravascular stent 300 is machined. The thickness of the non-conductive layer 340 can be optimized, by inspection or measurement, during the coating process for a specific material/apparatus combination. The patterning can be done via laser ablation, particularly using an ultra-short pulsed femto-second laser, or other techniques with the capability to achieve the electrode pattern having desired dimensions.

The laser ablation technique involves ablating the non-conducting mask material 340 such that a desired pattern is formed on the masked-electrode 350. A wide variety of laser systems can be used—from microsecond pulsed infrared $CO_2$ gas lasers at wavelengths between 9.3-11 μm to femto- to nanosecond pulsed excimer gas lasers in the 157-353 nm UV wavelength range (i.e., the nanosecond Argon fluoride (ArF) excimer laser systems, the nanosecond Xenon chloride (XeCl) excimer laser systems, or the femtoseond krypton fluoride (KrF) excimer laser systems) and femto- to nanosecond pulsed solid state lasers between wavelengths of 266-1060 nm (i.e. the nanoseond Er:YAG lasers in the mid-infrared wavelength region).

In one embodiment, a 1550 nm ultra-short pulse femtosecond laser is employed having an energy per pulse of about 50 μJ, plus about 5%, an average power of about 5 watts or 7.5 watts, a pulse width of less than 1.0 ps, typically about 850 fs, a peak power greater than about 50 MW, and a repetition rate of about 100 kHz to about 150 kHz. The pulse frequency used in laser ablation patterning varies with the solid-, liquid- or gas-state targets as they go through complex phase transitions during the application of high electrical energy. The laser ablation process employed has a repletion rate of 25 kHz, in one embodiment; alternatively, the laser ablation process has a repletion rate between about 1 to 50 kHz. A pattern resolution of 1-2 μm without any undesired heat-affected zone is achievable. Thus, the laser has the ability to ablate the mask material, leaving minimal to no heat effect or recast (cold ablation) and thus, allows for the preservation of dimensional features.

Cover gases may be used for patterning polymeric and ceramic based masks with femto-second lasing methods include argon, helium, and mixtures of the two. The absence of heat effect and the need to subject the laser patterned electrodes to subsequent finishing operations allow for quicker process turnaround times, better feature quality and dimensional retention and the opportunity to scale feature dimensions down to single to sub-micron scale. For femtosecond-, picosecond- and nanosecond-pulsing to be all applicable, chirped pulse amplification type (CPA) Ti-sapphire-based laser systems can be employed.

The micro-pattern 400 imparted on the masked electrode 350 should have feature sizes commensurate to the thickness of the non-conducting layer 340 for the layer to be machined properly. In general, the micro-pattern 400 imparted on the masked electrode 350 has a width W, a depth D, and a length L. The width W and depth D may be the same, and not vary, along the length L of the micro-pattern 400. Alternatively, the width W of the micro-pattern 400 may vary along the length L of the micro-pattern 400. Alternatively, the depth D of the micro-pattern 400 may vary along the length L of the micro-pattern 400. Alternatively, both the width W and the depth D of the micro-pattern 400 may vary along the length of the micro-pattern 400. The cumulative outer diameter of the patterned electrode 350 should be sized to ensure adequate contact between the intravascular stent 300 and the non-conducting mask 340 so that electrical current leakage between the contacting surfaces is minimal. The thickness of the non-conductive layer/mask 340 will measure on the same order of the feature size to be transferred to the inner diameter 301 of the stent 300. For example, a square-wave micro-pattern measuring 12 microns wide and 2 microns deep, which repeats every 24 microns, employs a non-conducting layer thickness nearly identical to the pattern feature size, i.e. a 2 micron thick layer on the electrode. Alternative thicknesses of the non-conductive layer/mask 340 may be used, for example, about 1-100 microns wide and/or 1-50 microns deep, which may repeat every 1-100 microns. The parameter will also vary with the specific length scale of micro-pattern 400 to be mounted. Alternatively, nano-sized patterns on implant surfaces will therefore also use similarly dimensioned features machined into the electrode mask.

Once the masked electrode 350 has been patterned, the intravascular stent 300, usually made of stainless steel, is mounted onto the masked electrode 350, positioned, and placed into an electrolyte for electrochemical micro-machining, as shown in FIG. 9. The intravascular stent may be made of any metal deemed biocompatible and eligible for use as Class I, II, or III medical device implants. For example, and not by way of limitation, the stent may be made of metal alloys of stainless steel, CoCr, Nitinol, MP35N, PtCr, or TaTi.

Through-mask ECμM 402 requires a better degree of tooling and process control compared to the conventional ECM technique. Thus, the selection of electrolyte is to be selected according to the extremely small gap between the tool and the workpiece. The masked electrode 350 and the inner diameter 301 of the stent 300 are circuited through the electrolyte flowing from masked electrode 350 to the inner diameter 301 of the stent 300. The electrolyte of choice should satisfy the requirements of being electrically conductive, being able to dissolve the electrode and intravascular stent materials, and being rendered passive in the absence of external power to drive the dissolution process. When considering the electrolyte, the following attributes are taken into account: water solvent based, neutral/acidic based, ability to machine the implant material, processing temperature range and capability, general electrode assembly with implant compatibility, whether reaction by-products are formed, and/or throwing power along and others that either are directly influenced or strongly interact with these mentioned.

In common micromachining processes, electrolytes have component(s) of KCl, unsaturated AgCl, NaCl, LiCl, $NaHCO_3$, NaOH, saline, $H_2SO_4$, HF, $H_3PO_4$, or/and other appropriate preparations. Depending on the intravascular stent material, the electrolyte of choice may range from concentrated forms of acids to dilute mixtures of neutral salt. In one embodiment, for example, the electrolyte used for implants made of a 316LVM stainless steel and L-605 alloy is an 85% phosphoric acid solution which has demonstrated useful ECM attributes and pattern transfer characteristics using a 1-5V regime at temperatures between 20-50° C. In another embodiment, the electrolyte is a LiCl/ethanol mixture. The selection of the electrolyte is dictated by the material of which the implant is made of.

Electrolytes for different alloys include the following: Iron-based alloys may use chloride based solutions in water; Ni-based alloys may use HCl based solutions or mixtures of brine and $H_2SO_4$; Ti-based alloys may use 10% HF+10% HCl+10% $HNO_3$ based solutions; Co—Cr—W-based alloys may use NaCl based solutions; WC-based alloys may use strong alkaline solutions; stainless steel and Co—Cr-based alloys may use phosphoric or chloride based solutions; and nitinol-based alloys may use sulfuric and LiCl based solutions. The electrolyte conductivity is dependent on a number of parameters, including: starting electrode distance, concentration of salt in the solution, local hydroxide concentration in electrolyte, bulk and local temperature, electrolyte flow rate, and the velocity of electrolyte. For stainless steel and CoCr based alloys, phosphoric or chloride based solutions have worked well. For Nickel Titanium alloys (Nitinol), sulfuric and LiCl based electrolytes have shown promise with results. In general, the electrolysis/dissolution of the metal during the machining process should only take place upon the application of an applied overpotential to ensure adequate control over machining characteristics. Thus the metal in the electrolyte is ideally rendered passive in the absence of external power to drive the dissolution process.

In electrochemical machining, electrical contacts to the intravascular stent/implant 300 and the metal electrode 380 are made, with the stent 300 being anode (+) and the metal electrode 380 being cathode (−). In conventional electrochemical machining, the shape of tool electrode defines the shape of workpiece product. Most of the machining takes place on the front end of the electrode since there is a stronger electrical field. However, as the tool machines into the workpiece, sidewalls of the tool also start facing the inner walls of the workpiece. This introduces an extra portion of the current distribution. The defined channels are essentially the conductive pathways through which dissolution will take place ion, which results in higher machining rates in the entrance sides. One embodiment disclosed herein overcomes this problem found in conventional machining by holding the anodic implant 300 at a fixed distance from the cathodic electrode 380. This distance is defined by the thickness of the non-conducting mask 340 on the cathodic electrode 380. A fixed inter-electrode gap is maintained, thus avoiding the problem of higher machining rates on the entrance sides of the electrode. The amount of cathodic surface area exposed is defined by the pattern to be transferred. Generally, it is good to start with a 1:1 cathode/anode surface are ratio, where the anodic surface area is the working surface of the implant. Specifically in this disclosure, the working surface is the luminal surface of the implant and thus, the area used for ratio calculations is derived from this surface only to avoid excessive current distributions.

The transfer accuracy of dimensional features from patterned electrode to the implant is dictated largely by the depth/time of the machining process relative to other feature dimensions targeted on the implant, like width. For example, if targeting 12 micron wide features on the implant using a 2-3 micron machining depth/time to resolve, one may target very close to 12 micron wide features on the electrode to be transferred due to minimal under-cutting of the mask/implant interface. The degree to which undercutting occurs (isotropic machining) is responsible for dimensional discrepancies that evolve over extended machining times. This is where the pulsing aspect attains the ideal cut surface qualities, but also aids in implementing more directional (anisotropic) machining to minimize discrepancies between electrode and implant pattern features. This is such that one achieves more of a 1:1 pattern transfer.

With reference to FIG. 9, the shape of the electrode 380 may be circular, tubular, ellipsoidal, and the like. Preferably, the metal electrode includes a circumference in the range of about 95% of the stent structure; more preferably, the metal electrode includes a circumference in the range of about 100% of the stent structure. The electrode 380 is disposed with its longitudinal axis being disposed substantially parallel with the longitudinal axis 316 of the intravascular stent 300.

Intravascular stents that are made of stainless steel are resistant against corrosion even upon moderate potentials, where its constituents should be dissolved from a thermodynamic perspective. In this passive region practically no electrochemical current is flowing; only at very positive potentials, in the transpassive region, ion transport sets in and the steel is anodically dissolved. Specifically, for 1.4301 stainless steel in 3 M HCl/6M HF electrolyte, the passivation peak is at around +0.2 $V_{Pd/H}$ and the passive region extends to about +1.5 $V_{Pd/H}$. In micro-machining, highly concentrated NaCl electrolytes or more 'aggressive' 3 M HCl/6M HF electrolyte can be used for dissolution of stainless steel at voltages of 10-40 V (low frequency AC) between the tool and the workpiece for pulse durations of 50-500 nanoseconds. With such adjustment, electrochemical micromachining by ultrashort voltage pulses is applicable.

The embodiments disclosed herein, therefore, disclose a process for the mass transfer or fabrication of micro-sized features on the inner diameter of an intravascular stent via Electrochemical Micro-Machining through an intravascular stent/metal electrode/non-conducting mask assembly.

Unlike other machining or pressing processes that impart micro-sized features one feature at a time, like directly writing micro-patterns onto the inner diameter using a laser, the fore-mentioned process imparts all desired features in one mass-transfer of the pattern, thus having the potential to reduce process cycle times tremendously. Another appealing aspect of this process is that there are no stresses imparted to the surface which could otherwise result in compromised mechanical performance of the stent with respect to fatigue and crack initiation. In addition, the ECµM parameters could be strategically adjusted to produce slightly rounded edges without the need for follow-up stress-relief processing.

While the present invention has been described with reference to its preferred embodiments, those of ordinary skill in the art will understand and appreciate that variations in structural materials, bioactive agents, etching methods, device configuration or device indication and use may be made without departing from the invention, which is limited in scope only by the claims appended hereto.

I claim:

1. A patterned masked electrode, comprising:
   a. A generally cylindrical electrically conductive electrode member having an outer surface, a first end, a second end and a stent mounting region intermediate the first end and the second end;
   b. A non-conductive coating on the outer surface of the electrode member; and
   c. A micro-pattern defined in the non-conductive coating passing through the non-conductive coating and exposing defined portions of the electrode member, the micro-pattern corresponding to a plurality of continuous elongate slots adapted to transfer electrical energy through the micro-pattern of a plurality of continuous elongate slots to a luminal surface of a stent positioned on the stent mounting region, and each of the plurality of continuous elongate slots extend along an entire longitudinal axis of the stent mounting region.

2. The patterned masked electrode of claim 1, wherein the non-conductive coating is of a material capable of being vacuum deposited onto the outer surface of the electrode member.

3. The patterned masked electrode of claim 1, further comprising an intraluminal stent concentrically engaged with the electrode member such that the non-conductive coating is intermediate the electrode member and the intraluminal stent.

4. The patterned masked electrode claim 1, wherein the non-conductive coating is made of a material capable of being applied to the electrode member by one of dipping, spray coating, air brushing or lamination techniques.

5. The patterned masked electrode claim 1, wherein the micro-pattern further comprises a plurality of grooves passing through the non-conductive coating, each of the plurality of grooves having a cross-sectional configuration selected from the group consisting of square, u-shaped, triangular, v-shaped, rectangular, keyway shaped.

6. The patterned masked electrode of claim 1, wherein each of the plurality of elongate slots of the micro-pattern has a width between about 2 and about 40µ and a pattern resolution of between about 1-2µ between adjacent elongate slots of the plurality of elongate slots.

7. An assembly, comprising:
   a. A generally cylindrical electrically conductive electrode member having an outer surface, a first end, a second end and an intermediate stent mounting region;
   b. A non-conductive coating on the outer surface of the electrode member;
   c. A micro-pattern of openings defined in and passing through the non-conductive coating; and the micro-pattern of openings exposing, through the micro-pattern of openings, defined elongate slot portions in the intermediate stent mounting region of the electrode member, the micro-pattern being configured to impart a pattern of grooves on a luminal surface of an intraluminal stent; and
   d. An intraluminal stent concentrically engaged around the non-conductive coating and positioned at the intermediate stent mounting region.

8. The assembly of claim 7, wherein the non-conductive coating is of a material capable of being vacuum deposited onto the outer surface of the electrode member.

9. The assembly of claim 7, wherein the micro-pattern corresponds to a pattern of grooves adapted to be transferred to a luminal surface of an intraluminal stent.

10. The assembly of claim 7, wherein the non-conductive coating is made of a material capable of being applied to the electrode member by one of dipping, spray coating, air brushing or lamination techniques.

11. The assembly of claim 7, wherein the micro-pattern further comprises a plurality of grooves passing through the non-conductive coating, each of the plurality of grooves having a cross-sectional configuration selected from the group consisting of square, u-shaped, triangular, v-shaped, rectangular, keyway shaped.

12. The assembly of claim 7, wherein the micro-pattern has a depth of approximately 0.5 µm-10 µm, a width of approximately 2 µm-40 µm.

* * * * *